US00PP26015P2

(12) United States Plant Patent
Kordes

(10) Patent No.: US PP26,015 P2
(45) Date of Patent: Oct. 27, 2015

(54) MINIATURE ROSE PLANT NAMED 'KORPOT036'

(50) Latin Name: *Rosa hybrida*
Varietal Denomination: KORpot036

(71) Applicant: Tim-Hermann Kordes, Klein Offenseth-Sparrieshoop (DE)

(72) Inventor: Tim-Hermann Kordes, Klein Offenseth-Sparrieshoop (DE)

(73) Assignee: W. Kordes' Söhne Rosenschulen GmbH & Co KG, Offenseth-Sparrieshoop (DE)

( * ) Notice: Subject to any disclaimer, the term of this patent is extended or adjusted under 35 U.S.C. 154(b) by 92 days.

(21) Appl. No.: 13/987,160

(22) Filed: Jul. 3, 2013

(51) Int. Cl.
*A01H 5/02* (2006.01)

(52) U.S. Cl.
USPC ..... Plt./117

(58) Field of Classification Search
USPC ..... Plt./117
CPC ..... A01H 5/0222
See application file for complete search history.

*Primary Examiner* — Keith O. Robinson

(57) ABSTRACT

A new and distinct variety of rose with long lasting, novel cream white flowers, and attractive foliage with good disease resistance. It exhibits compact growth with abundant flowers. The new variety propagates well from cuttings and by grafting. This new and distinct variety has shown to be uniform and stable in the resulting generations from asexual propagation.

1 Drawing Sheet

Latin name of genus and species: The botanical classification of the new rose plant is *Rosa hybrida.*

Variety denomination: The denomination of the new variety is 'KORpot036'.

CROSS REFERENCES AND FEDERAL R&D STATEMENT

There are no cross referenced or related applications. This variety was developed without the aid of any research grant.

BACKGROUND OF THE INVENTION

The present discovery constitutes a new and distinct variety of a miniature rose plant which was discovered in a cultivated area in my nursery June 2010. The new rose variety resulted from a naturally occurring mutation of unknown causation on a branch of 'KORcarubo', a non-patented rose variety from the same inventor.

The new rose plant was asexually propagated for further evaluation. This new and distinctive miniature rose variety is named 'KORpot036'.

SUMMARY OF THE DISCOVERY

The new rose plant 'KORpot036' may be distinguished from its parent, 'KORcarubo', by its cream white flower color.

The new and distinct rose plant was selected due to its:

1. Compact and uniform growth and flowering under greenhouse conditions when grown as a potted floral plant;
2. Abundant, long lasting, and attractive flowers and foliage;
3. Resistance to diseases encountered in greenhouse and nursery culture; and 4. Suitability for production from softwood cuttings in floral and nursery containers.

This combination of qualities is not present in prior rose cultivars known to the inventor. These objectives have been substantially achieved and in that distinguish 'KORpot036' from all other varieties of which we are aware.

As part of the rose evaluation program, Tim-Hermann Kordes asexually propagated the mutation by rooting cuttings, and conducted evaluations and observations on the resulting plants in a controlled environment in Offenseth-Sparrieshoop, Germany. The resulting seedlings exhibited distinctive physical and biological characteristics. The first asexual reproduction of 'KORpot036' was done by rooting softwood cuttings in a controlled environment in July 2010.

These initial and other subsequent propagations conducted in controlled environments show that the foregoing and all other characteristics of 'KORpot036' come true to form and are transmitted through succeeding generations.

BRIEF DESCRIPTION OF THE DRAWING

The accompanying color drawing shows as true as is reasonably possible to obtain in color photographs of this type, the typical characteristics of the buds, sepals, reproductive organs, flowers, leaves, prickles, and stems of 'KORpot036'.

DETAILED BOTANICAL DESCRIPTION

The following is a description of 'KORpot036', as observed growing in June 2013 in a nursery in British Columbia, Canada on plants of 3 months of age. Color references are made using The Royal Horticultural Society (London, England) Colour Chart, 2001 except where common terms of color are used.

For a comparison, several physical characteristics of the rose variety 'KORcarubo' are compared to 'KORpot036' in Chart 1.

CHART 1

| Characteristic | 'KORpot036' | 'KORcarubo' |
|---|---|---|
| General tonality on open flower | White Group N155D | Red-Purple Group 58C. |
| Basal petal spots (after opening, inner and outermost petals) | None observed | Green-Yellow Group 1C and Green-Yellow Group 1D |
| Incidence of prickles on stem | None observed | 5-8 per 10 cm of stem |

Parents:

*Parent*.—'KORcarubo'.

Classification:

*Botanical classification*.—*Rosa hybrida* 'KORpot036'.

*Commercial classification*.—Miniature rose.

FLOWER AND FLOWER BUD

Blooming habit: Recurrent. Floriferous.

Flower bud:

*Size*.—Upon opening, 20 mm in length from base of receptacle to distal end of bud and 12 mm diameter at its widest point.

*Bud form*.—Short. Pointed ovoid.

*Bud color*.—As sepals first unfold, bud color is Yellow-White Group 158B. When ¼ open, the upper surface of petals is Red Group 36D, and the lower surface is Red Group 36D. Guard Petals are Green-White Group 157A with slight intonations of Yellow-Green Group 145C along the veining.

*Sepals*.—Color: Upper surface Green Group 139A. Lower surface Green Group 137A. Size: Average 30-35 mm (l)×5-8 mm (w). Shape: Strong and serrated foliaceous appendages on 3 of the five sepals. Apex: Cirrose. Base: Flat at union with receptacle. Quantity: Five. Surface texture: Upper side: Smooth; lightly pubescent. Lower surface: Smooth; lightly pubescent. Stipitate glands: Limited number on underside and along margins.

Flower bloom:

*Fragrance*.—None.

*Duration*.—On the plant 12-16 days. Senesced petals drop away cleanly.

*Size*.—Medium for a miniature rose. When open, the average flower diameter is 40-45 mm and the average flower height is 25 mm.

*Form*.—Shape of flower when viewed from the side: Upon opening, upper part: Convex. Upon opening, lower part: Flattened convex. Open flower, upper part: Flat. Open flower, lower part: Flat.

Color:

*Upon opening, petals*.—Outermost petals: Outer Side: White Group N155C. Inner Side: White Group N155C. Innermost petals: Outer Side: Red Group 49D. Inner Side: Red Group 49D.

*Upon opening, basal petal spots*.—Average Size: 2.5-4 mm (h)×2.5-5 mm (w). Basal petal spot, outermost petals: Outer Side: Yellow-Green Group 145C. Inner side: Yellow-Green Group N144D. Basal petal spot, innermost petals: Outer Side: Yellow Green Group 145D. Inner side: Yellow Group 3B.

*After opening, petals*.—Outermost petals: Outer Side: White Group 155C. Inner Side: White Group 155C. Innermost petals: Outer Side: White Group N155B. Inner Side: White Group N155B.

*After opening, basal petal spots*.—No distinctive coloration at petal base observed.

General tonality: On open flower White Group N155D. No change in the general tonality at the end of the 3rd day. Afterwards, general tonality is White Group 155C.

Petals:

*Petal count*.—Double. Average range approximately 30-35 petals per flower under normal conditions.

*Petal reflex*.—Petals reflex slightly. Petal reflex occurs one at a time beginning with outermost petals.

*Petal margin*.—Entire.

*Petal shape*.—Obovate. Apex: Obtuse. Base: Obtuse.

*Petal size*.—25-28 mm (l)×20-25 mm (w).

*Thickness*.—Thin.

*Petal arrangement*.—Not formal.

*Texture*.—Outer Side: Smooth. Inner Side: Smooth.

Petaloids:

*Petaloid count*.—Average of 15-20 per flower.

*Petaloid size*.—15-20 mm (l)×10-15 mm (w).

*Petaloid color*.—Inner side: White Group N155D. Outer side: White Group N155D.

*Petaloid texture*.—Outer Surface: Smooth. Inner Surface: Smooth.

*Margins*.—Undulated.

*Petaloid shape*.—Highly irregular. Apex: Acute to obtuse. Base: Attenuate.

Reproductive organs:

*Pistils*.—Abundant. Approximately 70 present. Stigmas: Size: Diameter: 1 mm on average. Height: 2 mm on average. Location: Slightly inferior in position to anthers. Color: White Group 155A. Styles: Length: About 4 mm long. Color: Red-Purple Group 61B.

*Stamens*.—Approximately 70-80 on average and regularly arranged. Anthers: Size: Average 2 mm (l)×1 mm (w). Pollen: Generally present. Color: Greyed-Orange Group 163B. Filaments: Color: White Group 155B. Length: 5 mm.

Receptacle:

*Color*.—Green Group 143C.

*Shape*.—Urn-shaped.

*Texture*.—Smooth.

*Size*.—10 mm (h)×8 mm (w).

Peduncle:

*Surface*.—With stipitate glands.

*Length*.—30-40 mm average length.

*Diameter*.—5-7 mm average diameter.

*Color*.—Yellow-Green Group 144A.

*Strength*.—Strong.

*Texture*.—Smooth.

*Borne*.—One single flower per flower shoot. Flowers held upright.

THE PLANT

Growth: Vigorous growth.

Plant habit: Compact. Bushy. When grown as a 12 cm pot plant, the average plant height is 25-30 cm and the average plant width is 14 cm.

Stems:

*Length*.—150-250 mm average length.

*Diameter*.—4-8 mm average diameter.

*Stem color*.—Young wood: Yellow-Green Group 144A. Older wood: Not observed.

*Stem surface texture*.—Young Wood: Smooth.

*Laterals*.—Below initiation of inflorescence, laterals are non-flowering.

Prickles: None observed.

Leaves: Normally 3-5 leaflets on normal leaves in middle of the stem.

*Venation pattern*.—Pyramidal net pattern.

*Leaf size*.—65-75 mm (l)×50-60 mm (w).

*Abundance*.—Average.

Leaflets:

*Size*.—Average size of the terminal leaflet is 25-35 mm (l)×18-20 mm (w).

*Shape*.—Ovate. Base: Obtuse. Apex: Acute.

*Margins*.—Serrated.

*Surface*.—Semi-glossy.

*Texture*.—Upper side of leaflet: Smooth. Under side of leaflet: Smooth.

*Color, mature foliage*.—Upper Leaflet Surface: Green Group 137A. Lower Leaflet Surface: Green Group 137C.

*Color, juvenile foliage*.—Upper Leaflet Surface: Green Group 138A. Lower Leaflet Surface: Green Group 138B.

*Anthocyanin intonation*.—None observed.

*Arrangement*.—Odd pinnate.

*Venation*.—Reticulate.

Stipules:

*Size*.—8-10 mm (l)×3-4 mm (w).

*Stipule color*.—Green Group 137B.

*Anthocyanin*.—None observed.

*Margins*.—Limited stipitate glands present.

*Texture*.—Smooth.

*Shape*.—Apex: Apiculate. Base: Flat.

Petiole:

*Length*.—Average 10 mm.

*Diameter*.—Average 1 mm.

*Petiole color*.—Green Group 137B. Underneath: Green Group 138B.

*Margins*.—With very few stipitate glands.

*Anthocyanin*.—Greyed-Purple Group 183A.

*Prickles*.—None.

*Texture*.—Smooth.

Petiole rachis:

*Length*.—Average 20 mm.

*Diameter*.—Average 1 mm.

*Color*.—Green Group 137B.

*Anthocyanin*.—Greyed-Purple Group 183A.

*Margins*.—Limited number of stipitate glands on margins.

*Prickles*.—A few small prickles underneath.

*Texture*.—Smooth.

Hips/seed formation: None observed.

Winter hardiness: To date, the variety has been grown successfully in Zone 6.

Disease resistance: Above average resistance to Powdery mildew (*Sphaerotheca pannosa*) and Botrytis (*Botrytis cinerea*) diseases under normal growing conditions in British Columbia, Canada.

I claim:

1. A new and distinct variety of rose plant, as described and illustrated herein.

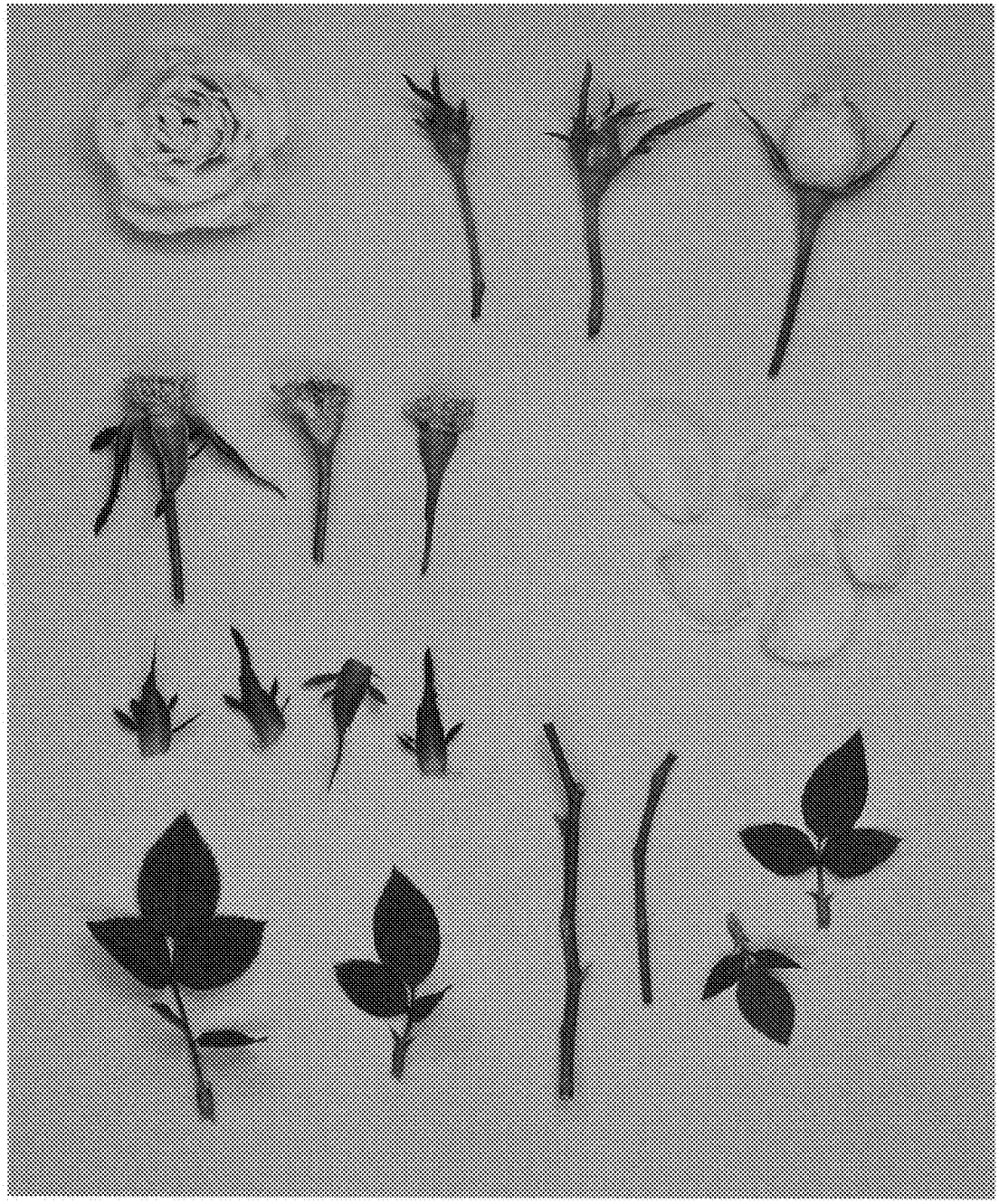

* * * * *